United States Patent [19]

Beck

[11] 3,987,076

[45] Oct. 19, 1976

[54] 2,6-DINITRO-3-THIOCYANATOANILINES

[75] Inventor: James R. Beck, Indianapolis, Ind.

[73] Assignee: Eli Lilly and Company, Indianapolis, Ind.

[22] Filed: June 23, 1975

[21] Appl. No.: 589,315

[52] U.S. Cl. .................... 260/454; 71/104; 424/302
[51] Int. Cl.² .................................. C07C 161/02
[58] Field of Search ............................ 260/454

[56] References Cited
UNITED STATES PATENTS 3,813,446   5/1974   Jacobs .............................. 260/454

FOREIGN PATENTS OR APPLICATIONS 43,935   1/1943   Japan .............................. 260/454

Primary Examiner—Lewis Gotts
Assistant Examiner—D. R. Phillips
Attorney, Agent, or Firm—Leroy Whitaker; Everet F. Smith

[57] ABSTRACT

A new class of 2,6-dinitroanilines bearing a thiocyanato group in the 3-position is disclosed. The new compounds possess activity against *Plasmopara viticola*, the causative organism of grape downy mildew.

4 Claims, No Drawings

2,6-DINITRO-3-THIOCYANATOANILINES

BACKGROUND OF THE INVENTION

1. Field of the Invention

This invention relates to a new class of 2,6-dinitroanilines. More particularly, this invention relates to 2,6-dinitroanilines having a thiocyanato group in the 3-position.

2. Description of the Prior Art

Various 2,6-dinitroanilines have been disclosed in the prior art. Borsche et al., C.A. 5, 2079 (1911); Hantzsch, *Deutsche Chemische Gesellschaft Berichte*, 43, 1662–1685 (1910); Joshi et al., C.A. 28, 469 (1934); and Daudt et al., U.S. Pat. No. 2,212,825 describe various 2,6-dinitroanilines. In the early 1960's, Soper disclosed that many 2,6-dinitroanilines possess herbicidal activity and he added many new compounds to the art. See, for example, U.S. Pat. Nos. 3,111,403; 3,257,190; 3,332,769; and 3,367,949. Following Soper's lead, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924; and Belgian Pat. No. 787,939.

SUMMARY OF THE INVENTION

I have discovered a new class of 2,6-dinitro-3-thiocyanatoanilines having the following structure:

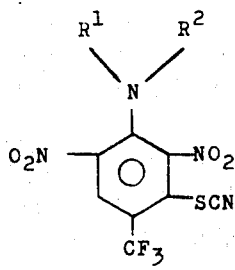

wherein $R^1$ is hydrogen, $C_1$-$C_4$ nontertiary alkyl, $C_3$-$C_4$ alkenyl, chloro $C_2$-$C_3$ alkyl, chloro $C_3$-$C_4$ alkenyl or cyclopropylmethyl;

$R^2$ is $C_1$-$C_7$ nontertiary alkyl, $C_3$-$C_4$ alkenyl, chloro $C_2$-$C_3$ alkyl, chloro $C_3$-$C_4$ alkenyl, cyclopropylmethyl or $N(R^3)_2$, and $R^3$ is $C_1$-$C_3$ alkyl;

provided that $R^2$ is $N(R^3)_2$ only when $R^1$ is hydrogen.

My novel compounds possess activity against *Plasmopara viticola*, the causative organism of grape downy mildew. They also exhibit herbicidal activity.

DESCRIPTION OF THE PREFERRED EMBODIMENT

In the above formula, all of the terms employed have the meanings normally ascribed to them in the chemical art. In order to illustrate the manner in which such terms are used, a few representative examples of compounds of my invention will be named.

N,N-diethyl-N'-(2,6-dinitro-3-thiocyanato-4-trifluoromethylphenyl)hydrazine

N-allyl-2,6-dinitro-N-n-propyl-3-thiocyanato-4-trifluoromethylaniline

N-cyclopropylmethyl-2,6-dinitro-N-ethyl-3-thiocyanato-4-trifluoromethylaniline

N-(2-butyl)-2,6-dinitro-3-thiocyanato-4-trifluoromethylaniline

N-(2-chloroethyl)-2,6-dinitro-N-n-propyl-3-thiocyanato-4-trifluoromethylaniline

N-(2-chloroallyl)-2,6-dinitro-N-ethyl-3-thiocyanato-4-trifluoromethylaniline 2,6-dinitro-N-ethyl-N-methallyl-3-thiocyanato-4-trifluoromethylaniline 2,6-dinitro-N-n-hexyl-N-methyl-3-thiocyanato-4-trifluoromethylaniline My compounds are readily prepared by the reaction of the corresponding 3-chloro-2,6-dinitroaniline with sodium sulfide and cyanogen chloride. The reaction is conveniently conducted in an inert solvent, such as dimethylformamide, dimethylacetamide, dioxane, or tetrahydrofuran, at a temperature within the range of about 10° C. to 40° C. and preferably at about 10° C. to 25° C. Cyanogen chloride may be bubbled into a solution of the chloro compound and sodium sulfide to effect the conversion. The reaction mixture is poured over ice to precipitate the product.

The 3-chloro-2,6-dinitroaniline starting material is conveniently prepared by the reaction of an appropriate amine with 2,4-dichloro-3,5-dinitrobenzotrifluoride in accordance with the procedure described in U.S. Pat. No. 3,617,252.

The preparation of my compounds will be further illustrated by the following example.

EXAMPLE 1

To a cold solution of 40 gm. of 3-chloro-2,6-dinitro-N-(3-pentyl)-4-trifluoromethylaniline in 400 ml. of dimethylformamide was added a solution of 36 gm. of sodium sulfide nonahydrate in 100 ml. of water. The mixture was stirred for one-half hour, then cyanogen chloride was bubbled into the cold solution for 10 minutes. At the end of this time, thin layer chromatography showed no starting material and the originally dark solution had become light red. The reaction mixture was poured over ice-water and the product solidified. It was recovered by filtration and recrystallized from 3A ethanol and water to yield 37 gm. (89%) of 2,6-dinitro-N-(3-pentyl)-3-thiocyanato-4-trifluoromethylaniline, m.p. 97°–99° C. The structure was confirmed by the NMR spectrum and elemental analysis.

Calculated: C, 41.27; H, 3.46; N, 14.81; Found: C, 41.02; H, 3.40; N, 14.56

Following the above procedure, the following additional representative compounds were prepared.

2,6-dinitro-N-methyl-3-thiocyanato-4-trifluoromethylaniline, m.p. 125°–126° C.

N,N-dimethyl-2,6-dinitro-3-thiocyanato-4-trifluoromethylaniline, m.p. 153°–155° C.

N'-(2,6-dinitro-3-thiocyanato-4-trifluoromethylphenyl)-N,N-dimethylhydrazine, m.p. 146°–148° C.

2,6-dinitro-N,N-di-n-propyl-3-thiocyanato-4-trifluoromethylaniline, oil

N,N-diethyl-2,6-dinitro-3-thiocyanato-4-trifluoromethylaniline, m.p. 116°–118° C.

Although the compounds of my invention exhibit some herbicidal activity, they will find their primary utility in the control of grape downy mildew. The compounds have exhibited quite good activity against *Plasmopara viticola*, the causative organism of this disease of grapes.

In accordance with standard agricultural practices, my compounds are preferably employed in liquid, powder, or dust compositions containing one or more of the active compounds. In preparing such compositions, the thiocyanato compounds can be modified with one or more of a plurality of additaments including organic solvents, petroleum distillates, water or other liquid carriers, surface active dispersing agents, and finely divided inert solids. In such compositions, my compounds can be present in a concentration from about 2 to 98% by weight.

In the preparation of dust compositions, my compounds can be formulated with any of the finely divided solids, such as pyrophyllite, talc, chalk, gypsum, and the like. In such operations, the finely divided carrier is ground or mixed with the compound or is wet with a solution of the compound in a volatile organic solvent. Similarly, dust compositions containing the active compound can be prepared with various solid surface active dispersing agents, such as fuller's earth, bentonite, attapulgite, and other clays. Depending upon the proportions of the ingredients, these dust compositions can be employed for the control of grape downy mildew or employed as concentrates and subsequently diluted with an additional solid surface active dispersing agent or with pyrophyllite, chalk, talc, gypsum, and the like to obtain the desired amount of active ingredient in a composition adapted to be employed for the control of grape downy mildew. Also, such dust compositions can be dispersed in water with or without the aid of dispersing agents to form liquid sprayable mixtures.

The thiocyanato compounds or a liquid or dust concentrate composition containing the active compound can be incorporated in intimate mixture with surface active dispersing agents, such as nonionic emulsifying agents, to form spray compositions. Such compositions may be employed as such or may be dispersed in liquid carriers to form diluted sprays containing the active compound in any desired amount.

Similarly, the active compounds can be formulated with a suitable water-immiscible organic liquid and a surface active dispersing agent to produce emulsifiable concentrates which can be further diluted with water and/or oil to form spray mixtures in the form of oil-water emulsions. Preferred dispersing agents to be employed in these compositions are oil-soluble and include the nonionic emulsifiers, such as condensation products of alkylene oxides with phenols, sorbitan esters, complex ether alcohols, and the like. Suitable organic liquids which can be employed include petroleum oils and distillates, toluene, and synthetic organic oils. The surface active dispersing agents are usually employed in liquid composition in the amount of from 0.1 to 20% by weight of the composition.

The exact concentration of the thiocyanato compound for use in the control of grape downy mildew can vary widely provided that an effective amount is applied to the host plant. The amount which is effective is dependent upon the particular compound employed and the severity of the infection. In general, good results are obtained using liquid compositions containing from about 2,000 to about 10 ppm. of the active compound. When dusts are used, good results are usually obtained with compositions containing from about 0.05 to about 5% or more by weight of the active compound. The compounds are preferably applied to grape foliage as a spray or dust at an application rate of from about 10 gm. to 2 kg. per hectare.

I claim:

1. A compound having the formula:

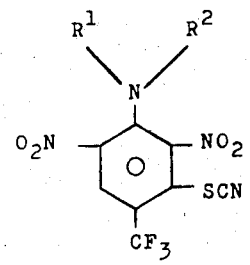

wherein
R$^1$ is hydrogen, C$_1$-C$_4$ nontertiary alkyl, C$_3$-C$_4$ alkenyl, chloro C$_2$-C$_3$ alkyl, chloro C$_3$-C$_4$ alkenyl or cyclopropylmethyl;
R$^2$ is C$_1$-C$_7$ nontertiary alkyl, C$_3$-C$_4$ alkenyl, chloro C$_2$-C$_3$ alkyl, chloro C$_3$-C$_4$ alkenyl, cyclopropylmethyl or N(R$^3$)$_2$, and
R$^3$ is C$_1$-C$_3$ alkyl;
provided that R$^2$ is N(R$^3$)$_2$ only when R$^1$ is hydrogen.

2. The compound of claim 1 which is N,N-dimethyl-2,6-dinitro-3-thiocyanato-4-trifluoromethylaniline.

3. The compound of claim 1 which is 2,6-dinitro-N,N-di-n-propyl-3-thiocyanato-4-trifluoromethylaniline.

4. The compound of claim 1 which is 2,6-dinitro-N-(3-pentyl)-3-thiocyanato-4-trifluoromethylaniline.

* * * * *